United States Patent [19]
Yamashita et al.

[11] 4,036,218
[45] July 19, 1977

[54] ENDOSCOPE

[75] Inventors: Nobuo Yamashita, Tama; Yoshisada Hayamizu, Hachiouji; Yoshitaka Nagai, Hachiouji; Toshihiro Imai, Hachiouji; Kazumasa Matsuo, Hachiouji, all of Japan

[73] Assignee: Olympus Optical Co., Ltd., Japan

[21] Appl. No.: 641,887

[22] Filed: Dec. 18, 1975

[30] Foreign Application Priority Data

Dec. 19, 1974 Japan .............................. 49-144948
Dec. 19, 1974 Japan .............................. 49-144949
Dec. 19, 1974 Japan .............................. 49-144950

[51] Int. Cl.² ............................................. A61B 1/00
[52] U.S. Cl. ......................................... 128/4; 350/69; 350/252

[58] Field of Search ........................................ 128/3-9; 350/54, 252, 69

[56] References Cited

U.S. PATENT DOCUMENTS

| 3,257,902 | 6/1966 | Hopkins | 350/54 |
| 3,414,344 | 12/1968 | Mukojima | 128/6 |
| 3,484,148 | 12/1969 | Gotoh | 350/54 |

Primary Examiner—Robert W. Michell
Assistant Examiner—Henry S. Layton
Attorney, Agent, or Firm—Cushman, Darby & Cushman

[57] ABSTRACT

An endoscope comprising optical elements such as field lenses and relay lenses arranged in an outer tube without using tubular spacers so that the intensity of transmitted light becomes high.

8 Claims, 14 Drawing Figures

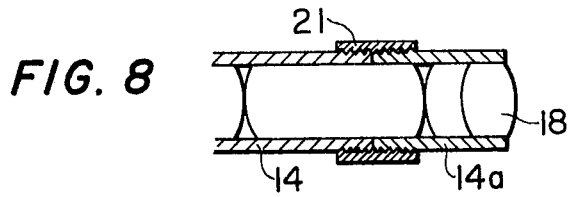
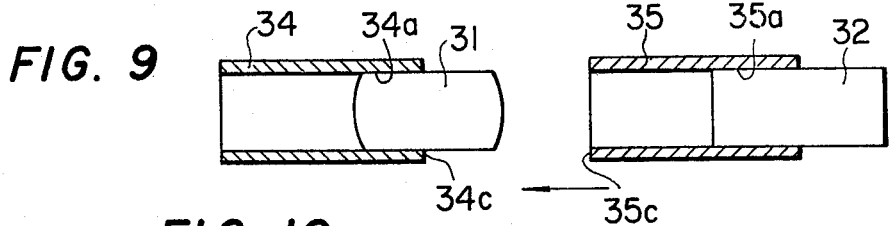
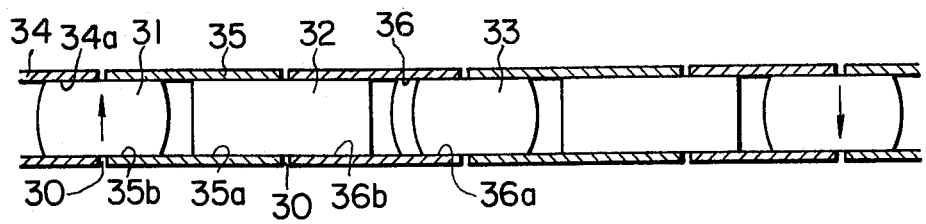
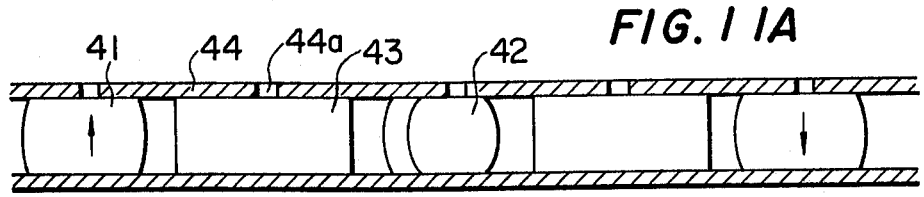
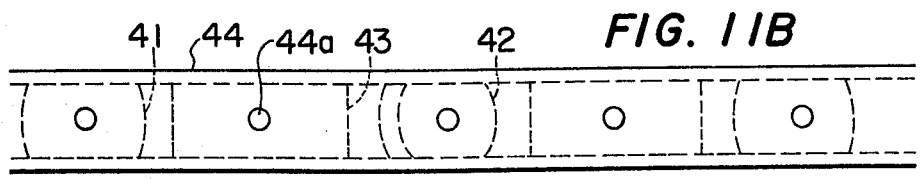
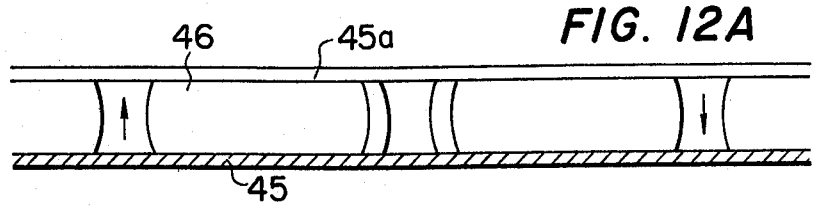
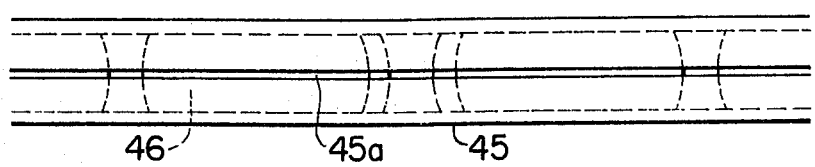

ENDOSCOPE

BACKGROUND OF THE INVENTION a. Field of The Invention

The present invention relates to an endoscope (not flexible) comprising an image-transmitting optical system which transmits an image in turn by a plural number of relay lenses.

b. Description of the Prior Art

An image-transmitting optical system used in endoscopes generally comprises, as shown in FIG. 1, field lenses 1 and imaging lenses 2 which are positioned alternately in an outer tube 4 with pre-determined airspaces by using tubular spacers 3 and is arranged to transmit an image in turn by means of said field lenses and imaging lenses. The intensity of transmitted light L transmitted by the above-mentioned image-transmitting optical system of known endoscopes is expressed by the following formula when reference symbol N represents the numerical aperture of the optical system and reference symbol A represents the area of transmitted image.

$$L \propto N^2 \times A$$

When the focal length of the optical system is represented by reference symbol $f$ and the effective diameter of the imaging lens 2 is represented by reference symbol $a_2$, the numerical aperture $N$ isexpressed by the following formula.

$$N \approx \frac{n\, a_2}{4f}$$

On the other hand, the area of transmitted image A is expressed by the following formula when the effective diameter of the field lens is represented by reference symbol $a_1$.

$$A = \pi(\frac{a_1}{2})^2$$

Therefore, the intensity of transmitted light L is expressed as follows.

$$L \propto \frac{n^2 a_1^2 a_2^2}{f^2}$$

For the above-mentioned image-transmitting optical system for known endoscopes, the intensity of transmitted light $L_0$ becomes as follows when the inner diameter of the tubular spacer is represented by reference symbol $a$, $$L_0 \propto \frac{a^4}{f^2}$$

because, $$a_1 = a_2 = a \text{ and } n = 1$$

As described in the above, for the image-transmitting optical system for known endoscopes, the intensity of transmitted light is limited by the focal length of the optical system and inner diameter of the tubular spacer and, therefore, it is difficult to obtain sufficient intensity of light.

If, however, it is possible to position respective lenses in such image-transmitting optical system for endoscopes without using the tubular spacers 3, effective diameters of both the field lenses 1 and imaging lenses 2 respectively become equal to outer diameters of respective lenses, and the intensity of transmitted light L in that case can be expressed by the following formula.

$$L \propto \frac{(m\,a)^2 \times (m\,a)^2}{f^2} = \frac{m^4 a^4}{f^2}$$

In the above, reference symbol $m$ represents the ratio between the inner diameter $a$ of the tubular spacer and outer diameter $b$ of the lenses, said ratio being $$m = \frac{b}{a}$$

It is, therefore, possible to increase the intensity of transmitted light to $m^4$ times compared with known endoscopes. When, for example, the inner diameter $a$ of the tubular spacers is 2.2 and the outer diameter $b$ of lenses is 2.5, it becomes $$m^4 = (\frac{b}{a})^4 = (\frac{2.5}{2.2})^4 = 1.668$$

and intensity of transmitted light becomes 1.668 times.

SUMMARY OF THE INVENTION

It is, therefore, a primary object of the present invention to provide an endoscope in which respective optical elements such as field lenses, relay lenses, etc. constituting the image-transmitting optical system are arranged in the outer tube without using tubular spacers.

Another object of the present invention is to provide an endoscope in which respective optical elements constituting the image-transmitting optical system are arranged in the outer tube without using tubular spacers by arranging respective optical elements into such image-transmitting optical system in which adjacent surfaces of respective optical elements contact each other.

Still another object of the present invention is to provide an endoscope in which respective optical elements constituting the image-transmitting optical system are respectively fixed to divided outer tubes and said outer tubes are connected in turn, the image-transmitting optical system being thus arranged by positioning respective optical elements in the outer tube without using tubular spacers.

Still another object of the present invention is to provide an endoscope in which small holes are provided to the outer tube at positions where respective optical elements constituting the image-transmitting optical system exist and respective optical elements are fixed to the outer tube by filling a binding agent through said small holes.

Still another object of the present invention is to provide an endoscope in which a slot is provided to the outer tube in the longitudinal direction of the outer tube and respective optical elements constituting the image-transmitting optical system are fixed to the outer tube by filling a binding agent through said slot.

BRIEF DESCRIPTION OF THE DRAWINGS

FIGS. 6 through 8 respectively show explanatory figures for explaining means for mounting an eyepiece of the endoscope to the outer tube of said first embodiment;

FIGS. 9 and 10 respectively show sectional views illustrating a second embodiment of the present invention, FIG. 9 showing the state before assembly, FIG. 10 showing the state after assembly;

FIGS. 11A and 11B respectively show a sectional view and plan view of a third embodiment of the present invention; and FIGS. 12A and 12B respectively show a sectional view and plan view of a fourth embodiment of the present invention.

DETAILED DESCRIPTION OF THE PREFERRED EMBODIMENTS

Figure 1:
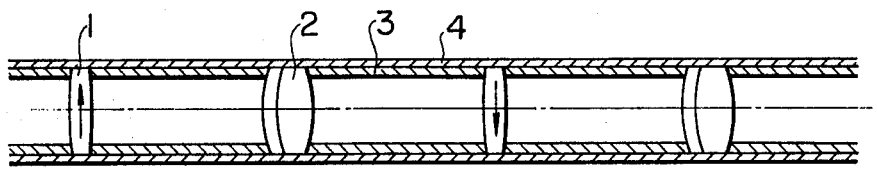
FIG. 1 shows a sectional view illustrating a part of known endoscope.
Figure 2:
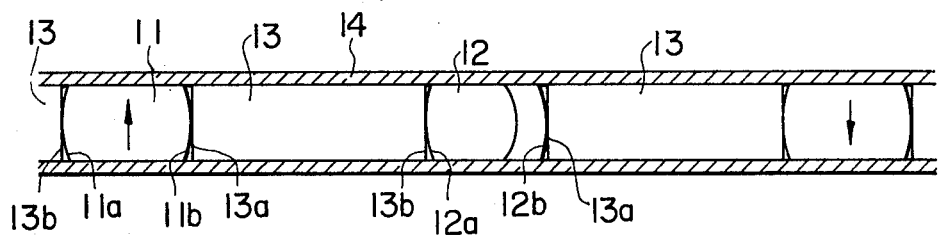
FIGS. 2 and 3 respectively show sectional views illustrating a first embodiment of the present invention.
Figure 3:
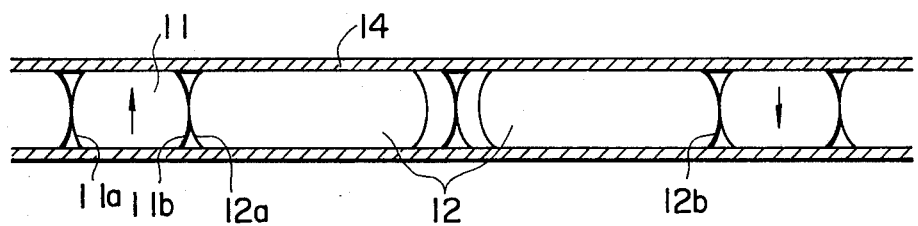

Referring to accompanying drawings, FIG. 2 and FIG. 3 respectively show the first embodiment of the present invention. The optical system shown in FIG. 2 comprises glass blocks with parallel planar surfaces each of which is arranged between an relay lens and field lens and serve for correction of astigmatism, increase of intensity of transmitted light for the image, and so forth. The optical system shown in FIG. 3 does not comprise said glass blocks with parallel planar surfaces. In said FIG. 2, numeral 11 designates a field lens, numeral 12 designates an imaging lens, and numeral 13 designates glass blocks with parallel planar surfaces. (In this specification, field lenses and imaging lenses are sometimes called relay lenses respectively and field lenses, imaging lenses and glass blocks with parallel planar surfaces are sometimes called optical elements respectively.) In the optical system shown in FIG. 2, field lenses 11, imagings lenses 12 and glass blocks with parallel planar surfaces 13 are respectively arranged in an outer tube 14 so that respective convex surfaces and planar surfaces which are adjacent to each other are all in contact with each other by their portions near the optical axis of the optical system. For example, a convex surface 11a of the field lens 11 contacts a planar surface 13b of a first glass block 13 and a convex surface 11b of said field lens 11 contacts a planar surface 13a of a second glass block 13. A convex surface 12a of the imaging lens 12 contacts a planar surface 13b of said second glass block 13 and a convex surface 12b of said imaging lens 12 contacts a planar surface 13a of a third glass block 13. Though FIG. 2 shows only a part of the optical system, such optical elements are of course arranged in turn like the example shown in FIG. 1 so that the image is transmitted in turn. In the example of the optical system shown in FIG. 3, glass blocks with parallel planar surfaces are not used and field lenses 11 and imaging lenses 12 are arranged alternately so that the image is transmitted in turn. In the optical system of the example shown in FIG. 3, respective optical elements are arranged in the outer tube 14 so that convex surfaces 11a and 11b on both sides of respective field lenses 11 respectively contact convex surfaces 12a and 12b on both sides of respective imaging lenses 12 so that said surfaces contact each other by their portions near the optical axis of the optical system like the example shown in FIG. 2. In the example shown in FIG. 3, each imaging lens 12 consists of two lens components. Therefore, convex surfaces of said lens components also contact each other.

In the endoscope having the image-transmitting optical system of lens arrangement as shown in FIGS. 2 or 3, respective optical elements can be positioned in the outer tube 14 by the method described below. That is, a lens to be positioned at one extreme end in the outer tube 14 is fixed at first by a means to be concretely described later. Then, respective optical elements such as lenses and glass blocks with parallel planear surfaces consituting the image-transmitting optical system are inserted one by one into the outer tube from the other end of the outer tube in the order of the arrangement of respective optical elements in the designed image-transmitting optical system. Thus, it is possible to properly position respective optical elements according to the above-mentioned lens arrangement. After inserting all necessary optical elements into the outer tube 14, the optical element which is inserted at last is fixed by an adequate means. Thus, it is possible to form an endoscope.

Figure 4:
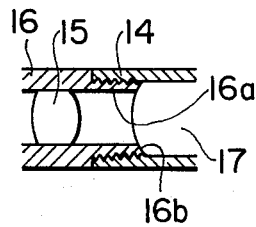
FIGS. 4 and 5 respectively show explanatory figures for explaining means for mounting an objective of the endoscope to the outer tube of said first embodiment.

Now, FIG. 4 shows an example of fixing means for the optical element at the end of the outer tube on the objective side out of fixing means for optical elements at both ends of the outer tube described in the above. In FIG. 4, numeral 16 designates a lens mount to which an objective 15 is fixed. The lens mount 16 is arranged to be mounted to the outer tube 14 by screwing the end 16a of the lens mount 16 into one end of the outer tube 14. In this example of fixing means, and end face 16b on one end of the lens mount 16 for the objective is utilized as the standard position for the optical element 17 which is arranged at the position closest to the objective in the image-transmitting optical system. When the lens mount 16 for the objective is fixed at first to one end of the outer tube 14 as described in the above and respective optical elements are then inserted in turn into the outer tube 14 from the other end of the outer tube 14 as described already, it is possible to obtain the lens arrangement as shown in FIG. 2 or 3. Here, as the method for mounting the lens mount 16 for the objective to the outer tube 14, a binding agent may be adopted instead of screwing.

Figure 5:
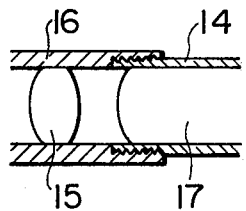

As the fixing means for the above-mentioned optical element on the objective side, it is also possible to adopt the means to fix the optical element, which is arranged closest to the objective in the outer tube 14, directly to the outer tube 14 by a binding agent. In this case, the method for mounting the lens mount 16 for the objective to the outer tube 14 is not limited to the above-mentioned method shown in FIG. 4. That is, as shown in FIG. 5 for example, it is also possible to screw the lens mount 16 for the objective onto the outer surface of the end of the outer tube 14 or to fix by using a binding agent.

Figure 6:
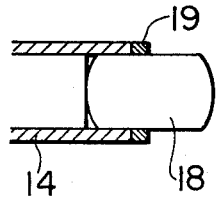
Figure 7:
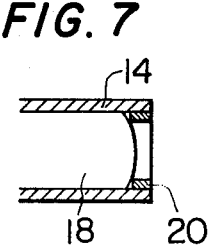

When the optical element at the other end of the outer tube, i.e., on the eyepiece side, is fixed to the outer tube after inserting respective optical elements into the outer tube by the above-mentioned method, an endoscope is formed. Means for fixing the optical element on the eyepiece side to the outer tube are described below. One of said means is to fix the optical element 18 by using a binding agent 19 as shown in FIG. 6. In this means, however, it is impossible to take out respective optical elements from the eyepiece side, when any breakage is caused in the outer tube, because it is impossible to dismount the optical element 18 and respective optical elements should be taken out only from the objective side. This is very inconvenient. If the optical element on the objective side is also fixed in the above case, it becomes impossible to take out respective optical elements at all. An alternative means which eliminates the above-mentioned disadvantage is to employ a fixing ring 20 as shown in FIG. 7. Said means shown in FIG. 7, however, has a disadvantage that an eclipse of the image occurs. In practice, it is difficult to obtain accurate alignment of optical elements in case of this kind of image-transmitting optical systems and, therefore, the diameter of the image is made about 2.3 when, for example, the lens diameter is 2.8. Therefore, the eclipse of the image will be prevented when a thin fixing ring of thickness about 0.15 is used. Moreover, at the position near this last lens, the image is stopped down to some extent. Therefore, in combination with the above-mentioned thin retaining ring, the problem of eclipse has almost no influence on performance in actual use. However, by the most preferable fixing means described in the following, it is possible to eliminate the above-mentioned two disadvantages. That is, in said most preferable means, the end portion of the outer tube 14 is divided into two portions, i.e., portionns 14 and 14a. The optical element 18 closest to the eyepiece is fixed into one portion 14a of the outer tube by using a binding agent. Then both portions 14 and 14a are coupled and fixed to each other by using a coupling ring 21. By this means, any eclipse of the image is not caused at all and, moreover, it is very convenient for repair at the time of breakage in the inside because said two portions of the outer tube can be easily disconnected from each other.

In the above-mentioned embodiments, it is desirable when assembling to insert respective optical elements in turn by feeding dry gas such as nitrogen ($N_2$) in order to prevent condensation of moisture which may otherwise be caused at such portions where respective optical elements contact each other.

Now, a second embodiment of the present invention is described referring to FIG. 9. In FIG. 9, numeral 31 designate a relay lens (field lens) and numeral 34 designates an outer tube which holds the lens 31. Unlike the outer tube 14 of the first embodiment, the outer tube 34 is formed by a short tube of a pre-determined length to be described later and said lens 31 is fixed to a portion 34a near one end of the outer tube 34 by using a binding agent. As it is evident from FIG. 9, one end portion of the lens 31 projects from the outer tube 34. Numeral 32 designates a glass block with parallel planar surfaces and numeral 35 designates an outer tube for fixing said glass block with parallel planar surfaces. In the same way as fixing of the lens 31 mentioned in the above, the glass block 32 is fixed to the outer tube 35 by binding one end portion of the glass block 32 to one end portion 35a of the outer tube 35 by a binding agent so that the other end of the glass block will project from the outer tube 35.

All optical elements constituting the image-transmitting optical system are respectively fixed to separate outer tubes by the above-mentioned fixing method. Then, respective optical elements fixed to respective outer tubes are combined according to the arrangement of the designed optical system. That is, when a glass block 32 with parallel planar surfaces is to be combined next to the field lens 31 shown in FIG. 9, the portion of the outer tube 35 where the glass block 32 with parallel planar surfaces does not exist may be fitted onto the portion of the lens 31 which projects from the outer tube 34 by moving the outer tube 35 as shown by an arrowhead in FIG. 9 so that the outer tube 35 covers the lens 31. In the same way, to the portion of the outer tube 34 where the lens 31 does not exist, a right portion of, for example, a glass block with parallel planar surfaces which is to be positioned on the left side of the lens 31 is inserted and combined. In that case, on the left portion of said glass block to be inserted, an another outer tube similar to the illustrated outer tube is of course fixed. Besides, on the right portion of the glass block 32 with parallel planar surfaces shown in FIG. 9 which was combined to the lens 31 as described in the above, another lens which should come to the right side of the glass block 32, for example an imaging lens, is combined in the same way. The second embodiment of the present invention is arranged to form the designed image-transmitting optical system by combining the pre-determined optical elements as described in the above and fixing both ends of said image-transmitting optical system by an adequate means. By the above arrangement, it is possible to arrange respective optical elements such as relay lenses constituting the image-transmitting optical system in the long outer tube without using tubular spacers.

FIG. 10 shows a part of the endoscope according to the second embodiment of the present invention in which respective optical elements are arranged in turn as described in the above. In the embodiment shown in FIG. 10, slight spaces 30 are provided between adjacent portions of outer tubes 34, 35, 36 and so on to which respective optical elements 31, 32, 33 and so on are fixed. By filling a binding agent through these spaces 30, it is possible to fix those portions of respective optical elements, which had been projected from respective outer tube, to portions 35b, 36b and so on of respective outer tubes where respective optical elements are not yet fixed by a binding agent, the image-transmitting optical system as a whole being thus fixed integrally and securely. In this case, it is of course necessary to accurately decide the length of respective outer tubes and positions where respective optical elements are to be fixed by a binding agent so that airspaces between respective optical elements including spaces 30 will become equal to design values.

If, in said second embodiment, respective optical elements are fixed too firmly to respective outer tubes by filling a binding agent through spaces 30, it will become impossible to exchange the optical element in the endoscope when an optical element is broken. Therefore, it is preferable to use a binding agent for which binding strength is not so high. To facilitate exchange of optical elements at the time of repair, it is more preferable to combine adjacent outer tubes so that their adjacent end faces (end faces 34c, 35c, etc. in FIG. 9) will closely contact each other without providing air spaces 30 and to fix both ends of the image-transmitting optical system by adequate means after combining all outer tubes. Thus, it is possible to securely fix all outer tubes, which are carrying respective optical elements, integrally without using a binding agent. At the time of repair, the image-transmitting optical system can be disassembled by disconnecting the fixed end portions of respective outer tubes and, therefore, broken optical elements can be replaced easily. Moreover, in this case, it is possible to disassemble only the particular portion where replacement is required. When spare optical elements fixed to outer tubes as shown in FIG. 9 and having the shapes and dimentions same as those of optical elements to be replaced are prepared beforehand, it is possible to repair the broken portion by replacing the broken optical element with such spare optical element.

FIG. 10 shows an example of the image-transmitting optical system according to the second embodiment. It is of course possible to apply the second embodiment in the same way to such image-transmitting optical system in which glass blocks with parallel planar surfaces are not used. As for the position for fixing the lens or glass block with parallel planar surfaces to the outer tube as shown in FIG. 9, it is preferable to fix so that the end face of the outer tube comes to the middle of the lens or glass block with parallel planar surfaces because the strength then becomes highest.

Now, FIGS. 11A and 11B respectively show a third embodiment of the present invention. FIG. 11A shows a sectional view of the third embodiment and FIG. 11B shows the third embodiment which is seen from the above in FIG. 11A. In these figures, numeral 41 designates a field lens, numeral 42 designates an imaging lens, numeral 43 designates a glass block with parallel planar surfaces and numeral 44 designates an outer tube. As shown in these figures, the outer tube 44, to which respective optical elements are inserted, has small holes 44a formed at those positions where these optical elements are to be arranged. This embodiment is arranged to insert respective optical elements to those positions of corresponding small holes 44a and, then, to fix those optical elements to the desired positions of the outer tube 44 by filling a binding agent utilizing these small holes 44a. Therefore, it is necessary to coincide the positions of said small holes 44a, which are formed in the outer tube 44, with the positions where respective relay lenses and glass blocks with parallel planar surfaces constituting the optical system are to be arranged. FIGS. 11A and 11B show an example in which each one small hole is provided at the position where each optical element is to be fixed. It is, however, also possible to further provide another small hole at the position opposite to each of said small holes i.e., on the bottom side in FIG. 11A, each two small holes being then provided at the position of each optical element. Besides, the number of small holes for each optical element may be increased to three, four and so on. When the number of small holes for fixing each optical element becomes larger, respective optical elements can be fixed to the outer tube more securely but the strength of the outer tube itself becomes lower.

A fourth embodiment of the present invention is shown in FIGS. 12A and 12B. FIG. 12A shows a sectional view of the fourth embodiment and FIG. 12B shows the fourth embodiment seen from above in FIG. 12A. In this embodiment, an outer tube 45 has a slot 45a which is formed in the longitudinal direction of the outer tube 45. When respective optical elements 46 are arranged at pre-determined positions in the outer tube 45 having the slot 45a and a binding agent is then filled through the slot 45a, it is possible to fix respective optical elements at pre-determined positions in the outer tube. In case of said fourth embodiment, it is possible to fix each optical element to the outer tube by the length approximately equal to the length of the optical element and, therefore, it is possible to securely fix respective optical elements even when the number of the slot is only one. It is not preferable to provide a plural number of slots because the strength of the outer tube will become low.

The fix respective optical elements at pre-determined positions in the outer tube in these third and fourth embodiments, respective optical elements may be inserted and fixed in turn by using barlike jigs. When lengths of respective bar-like jigs are accurately decided according to positions where respective optical elements are to be arranged, it is possible to accurately position respective optical elements.

As described in the above referring to respective embodiments, for the endoscope according to the present invention, respective optical elements are arranged at pre-determined positions in the outer tube without using tubular spacers. That is, in the first embodiment, respective optical elements constituting the image-transmitting optical system are arranged so that their adjacent surfaces contact each other. Thus, all optical elements are arranged at proper positions in the outer tube by fixing only those optical elements, which are positioned at both ends of the outer tube, to the outer tube. In the second embodiment, the outer tube is divided into plurality of short outer tubes, respective optical elements are fixed to respective short outer tubes and, then, plurality of short outer tubes to which optical elements are fixed are connected together so that an endoscope is formed without using tubular spacers. In the third and fourth embodiments, the outer tube has small holes or a slot formed in it and respective optical elements are fixed by a binding agent at pre-determined positions in the outer tube by utilising said small holes or slot so that an endoscope is formed without using tubular spacers.

As tubular spacers are not used in any embodiment of the endoscope according to the present invention as described in the above, the present invention provides an endoscope for which intensity of transmitted light is extremely higher compared with known endoscopes comprising tubular spacers.

Besides, in known endoscopes comprising tubular spacers, errors in lengths of tubular spacers and respective optical elements in the direction of the optical axis are accumulated and, consequently, a comparatively large error is sometimes caused for the image-transmitting optical system as a whole. On the contrary, in the present invention, the above-mentioned error is extremely small and, therefore, it is possible to obtain an endoscope having high accuracy. Moreover, the endoscope according to the present invention can be assembled easily and, even when an optical element is broken by mistake, the broken optical element can be replaced easily.

We claim:

1. An endoscope having an objective side and an eyepiece side and comprising optical elements constituting an image-transmitting optical system and an outer tube for holding said optical elements therein, said image-transmitting optical system being arranged so that respective adjacent surfaces of respective optical elements contact each other and two optical elements positioned at both ends of said outer tube out of said optical elements are respectively fixed to said outer tube.

2. An endoscope according to claim 1 further comprising a lens mount holding an objective, one end of said lens mount being inserted and fixed into one end of said outer tube, one of said optical elements positioned at the end of said outer tube on the objective side being fixed by means of the end face of said one end of said lens mount inserted into said outer tube.

3. An endoscope according to claim 1, in which one of said optical elements positioned at the end of said outer tube on the eyepiece side is slightly projected from the end face of the outer tube on the eyepiece side and the end face of the outer tube on the eyepiece side is fixed to the side surface of said projected optical element by means of a binding agent.

4. An endoscope according to claim 1, in which said optical element positioned at the end of said outer tube on the eyepiece side is fixed by means of a fixing ring.

5. An endoscope according to claim 1 further comprising a short outer tube for holding said optical element positioned at the end of said outer tube on the eyepiece side, said short outer tube being connected to said outer tube after fixing said optical element positioned at the end of said outer tube on the eyepiece side to said short outer tube.

6. An endoscope comprising optical elements constituting an image-transmitting optical system and an outer tube for holding said optical elements therein, in which said outer tube is divided into a plural number of short outer tube portions and said optical elements are respectively fixed to said short outer tube portions so that one end portion of each optical element projects from the corresponding short outer tube portion, said short outer tube portions carrying respective optical elements being connected by inserting the projected end portion of each optical element into the adjacent short outer tube portion in turn.

7. An endoscope comprising optical elements constituting an image-transmitting optical system and an outer tube for holding said optical elements therein, in which said outer tube has small holes respectively formed at positions where respective optical elements are arranged in said outer tube and said respective optical elements are fixed to said outer tube by filling a binding agent through said small holes.

8. An endoscope comprising optical elements constituting an image-transmitting optical system and an outer tube for holding said optical elements therein, in which said outer tube has a slot formed in the longitudinal direction of said outer tube and said respective optical elements are fixed to said outer tube by filling a binding agent through said slot.

* * * * *